US012661105B2

(12) United States Patent
Dooney, Jr. et al.

(10) Patent No.: US 12,661,105 B2
(45) Date of Patent: Jun. 23, 2026

(54) ADJUSTABLE TISSUE REPAIR SYSTEMS AND SURGICAL METHODS

(71) Applicant: ARTHREX, INC., Naples, FL (US)

(72) Inventors: Thomas Dooney, Jr., Naples, FL (US); Matthew John Ravenscroft, Congleton (GB)

(73) Assignee: ARTHREX, INC., Naples, FL (US)

( * ) Notice: Subject to any disclaimer, the term of this patent is extended or adjusted under 35 U.S.C. 154(b) by 232 days.

(21) Appl. No.: 18/240,568

(22) Filed: Aug. 31, 2023

(65) Prior Publication Data

US 2025/0072883 A1 Mar. 6, 2025

(51) Int. Cl.
*A61B 17/04* (2006.01)

(52) U.S. Cl.
CPC .. *A61B 17/0401* (2013.01); *A61B 2017/0409* (2013.01); *A61B 2017/0464* (2013.01); *A61B 2017/0496* (2013.01)

(58) Field of Classification Search
CPC ........ A61B 17/0401; A61B 2017/0409; A61B 2017/0414; A61B 2017/0464; A61B 2017/0496
See application file for complete search history.

(56) References Cited

U.S. PATENT DOCUMENTS

| | | | |
|---|---|---|---|
| 6,767,037 B2 | 7/2004 | Wenstrom, Jr. | |
| 7,585,311 B2 | 9/2009 | Green et al. | |
| 8,100,942 B1 | 1/2012 | Green et al. | |
| 8,109,969 B1 | 2/2012 | Green et al. | |
| 8,231,654 B2 * | 7/2012 | Kaiser .............. | A61B 17/06166 606/232 |
| 8,267,964 B2 | 9/2012 | Green et al. | |
| 9,060,764 B2 | 6/2015 | Sengun | |
| 9,144,425 B2 | 9/2015 | Kaplan | |
| 9,737,293 B2 | 8/2017 | Sengun et al. | |
| 10,123,792 B2 | 11/2018 | Pilgeram | |
| 10,136,886 B2 * | 11/2018 | Norton ............. | A61B 17/06166 |
| 10,729,423 B2 | 8/2020 | Kaiser et al. | |
| 10,743,856 B2 | 8/2020 | Durando | |
| 10,835,231 B2 | 11/2020 | Hernandez et al. | |
| 10,912,549 B2 | 2/2021 | Sengun et al. | |
| 11,039,827 B2 | 6/2021 | Sengun et al. | |
| 2007/0219558 A1 | 9/2007 | Deutsch | |
| 2011/0213416 A1 * | 9/2011 | Kaiser ................ | A61B 17/0401 606/232 |
| 2013/0144338 A1 * | 6/2013 | Stone ................. | A61B 17/0401 606/232 |
| 2015/0297211 A1 * | 10/2015 | Sullivan ............. | A61B 17/0401 606/232 |
| 2017/0071590 A1 | 3/2017 | Macleod | |
| 2017/0209135 A1 * | 7/2017 | Sullivan ............. | A61B 17/0483 |
| 2017/0209139 A1 * | 7/2017 | Burkhart ............ | A61B 17/0401 |
| 2017/0273680 A1 | 9/2017 | Sengun et al. | |

(Continued)

*Primary Examiner* — Dianne Dornbusch

(74) *Attorney, Agent, or Firm* — Carlson, Gaskey & Olds, P.C.

(57) ABSTRACT

Adjustable tissue repair systems and methods are provided for reducing and fixating tissue to bone. The proposed systems and methods utilize two or more suture anchors and one or more adjustable suture loops for reducing and fixating the tissue to the bone. The suture anchors may be positioned as part of a multi-row fixation technique for providing a desired area of footprint compression over top of the tissue.

22 Claims, 11 Drawing Sheets

(56)                    References Cited

U.S. PATENT DOCUMENTS

2018/0221010  A1*    8/2018  Lund .................. A61B 17/0401
2020/0170634  A1*    6/2020  Burkhart .............. A61F 2/0811
2020/0178952  A1     6/2020  Sengun

* cited by examiner

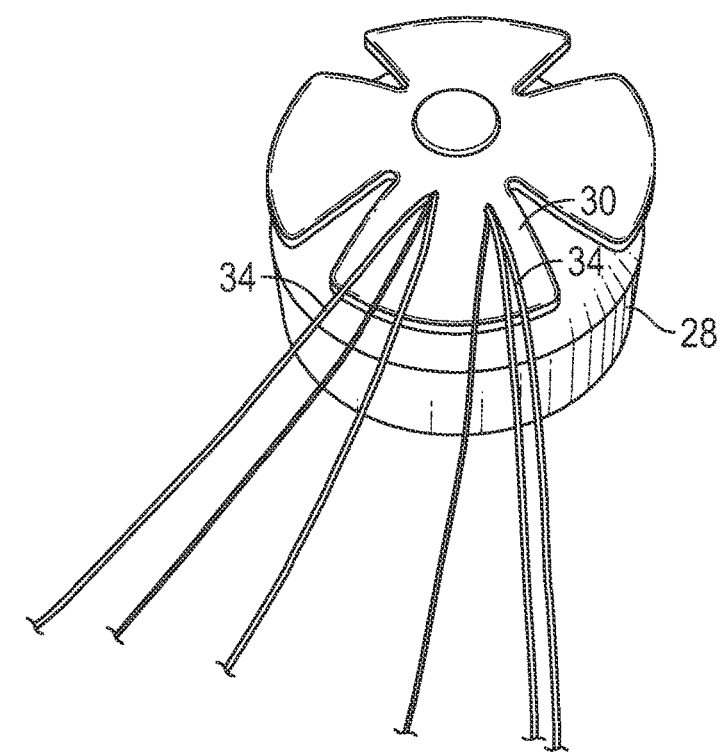
FIG. 7
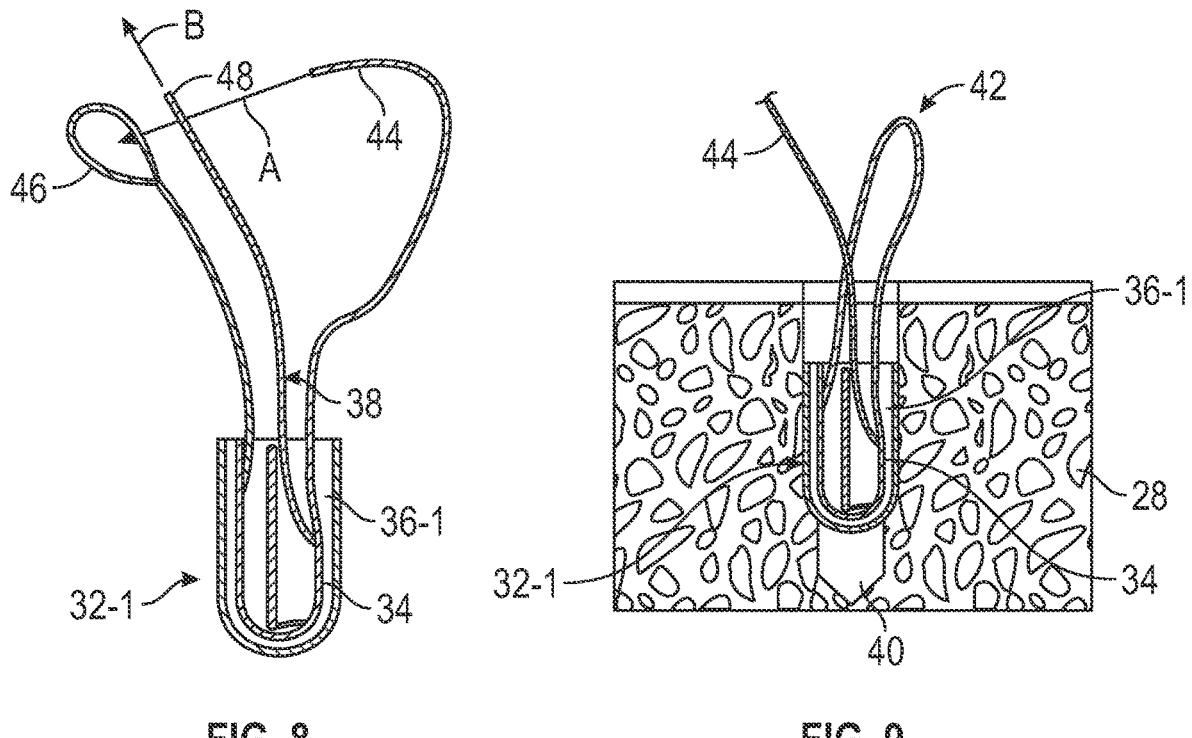
FIG. 8  FIG. 9

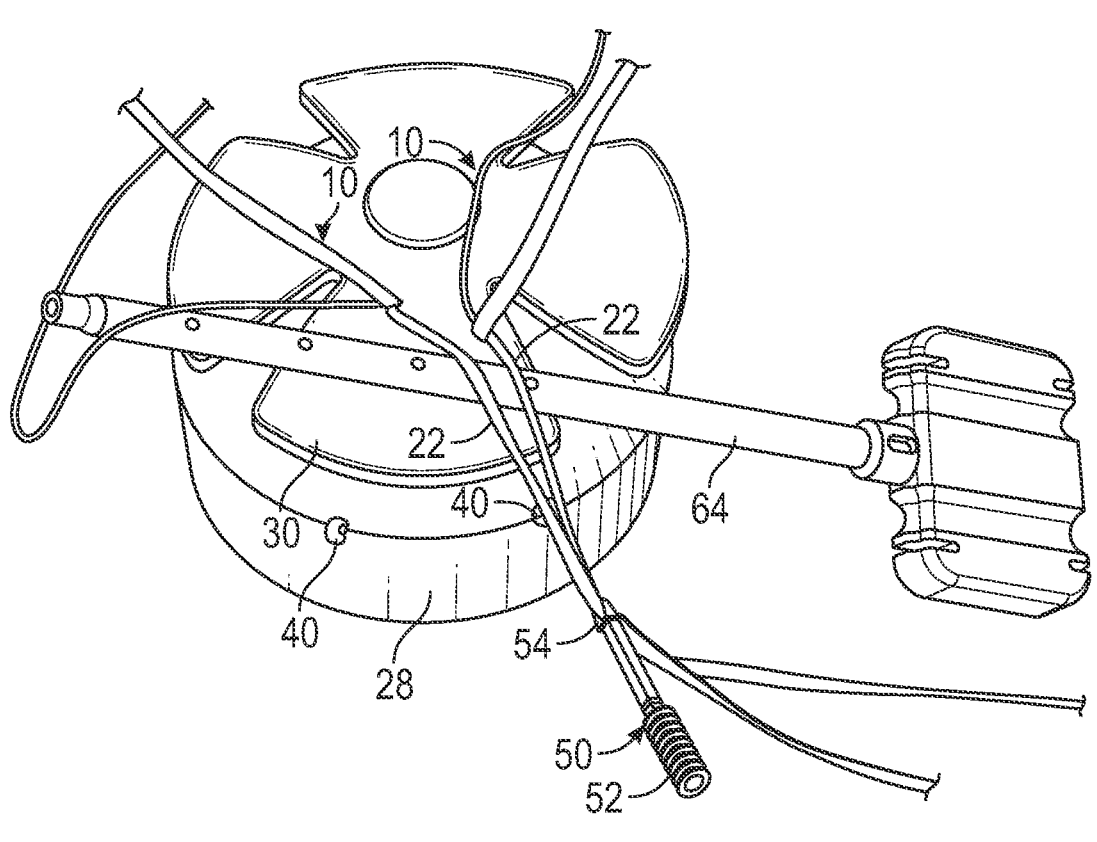
FIG. 16
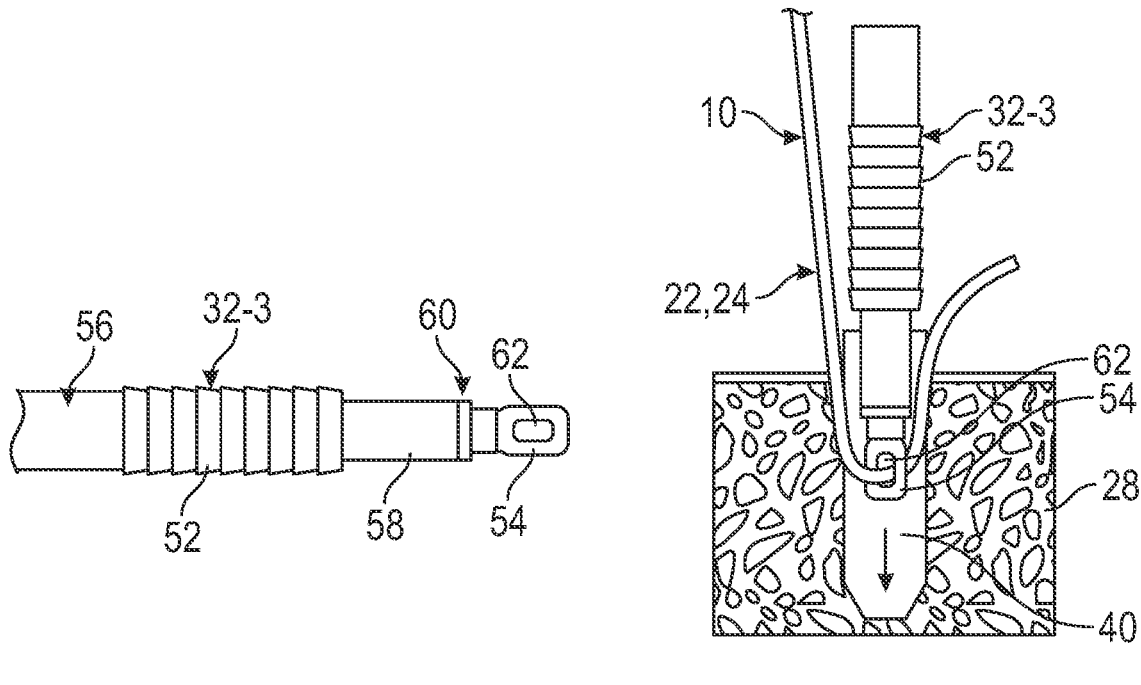
FIG. 17                    FIG. 18

66

32,50

| Suture Anchors | 12,14

Suture Strands and Needle |

68

Tools (Drills, Guides, Punches, Taps, etc)

FIG. 23

ADJUSTABLE TISSUE REPAIR SYSTEMS AND SURGICAL METHODS

BACKGROUND

This disclosure relates to the field of surgery, and more particularly to systems and associated surgical methods for reducing, fixating, and compressing tissue relative to bone.

Repetitive trauma to a joint, such as a knee, ankle, hip, or shoulder joint, for example, may result in the development of tissue defects (e.g., soft tissue tears, cartilage defects, etc.). If not treated, tissue defects could further deteriorate, thereby causing joint instability and discomfort.

SUMMARY

This disclosure relates to adjustable tissue repair systems and methods for reducing and fixating tissue to bone. The proposed systems and methods utilize two or more suture anchors and one or more adjustable suture loops for reducing and fixating the tissue to the bone. The suture anchors may be positioned as part of a multi-row fixation technique for providing a desired area of footprint compression over top of the tissue.

An exemplary surgical method may include, inter alia, inserting a first suture anchor into a bone, passing a first suture of the first suture anchor through a tissue, feeding the first suture through a loop of a first adjustable suture loop, securing the first adjustable suture loop relative to the first suture anchor, connecting a first limb of the first adjustable suture loop to a second suture anchor, and inserting the second suture anchor into the bone at a position that is lateral to the first suture anchor.

Another exemplary surgical method may include, inter alia, inserting a first suture anchor into a bone, passing a first suture of the first suture anchor through a tissue, feeding the first suture through a loop of a first adjustable suture loop, knotlessly securing the first adjustable suture loop relative to the first suture anchor, tensioning the first suture to approximate the first adjustable suture loop against the tissue, connecting a first limb of the first adjustable suture loop to a second suture anchor, and inserting the second suture anchor into the bone at a position that is lateral to the first suture anchor, thereby fixating the first limb relative to the bone such that the first limb extends over top of the tissue.

An exemplary adjustable tissue repair system may include, inter alia, a first knotless suture anchor, a second knotless suture anchor, and an adjustable suture loop connected to both the first knotless suture anchor and the second knotless suture anchor. The adjustable suture loop includes a loop, a slidable limb, and a static limb.

The embodiments, examples, and alternatives of the preceding paragraphs, the claims, or the following description and drawings, including any of their various aspects or respective individual features, may be taken independently or in any combination. Features described in connection with one embodiment are applicable to all embodiments, unless such features are incompatible.

The various features and advantages of this disclosure will become apparent to those skilled in the art from the following detailed description. The drawings that accompany the detailed description can be briefly described as follows.

BRIEF DESCRIPTION OF THE DRAWINGS

FIG. 7 illustrates another step of a surgical method for reattaching torn tissue to bone.

FIGS. 8 and 9 illustrate an exemplary knotless suture anchor.

FIG. 16 illustrates another step of a surgical method for reattaching torn tissue to bone.

FIGS. 17 and 18 illustrate another exemplary knotless suture anchor.

FIG. 23 schematically illustrates an exemplary adjustable tissue fixation system.

DETAILED DESCRIPTION

Figure 1:
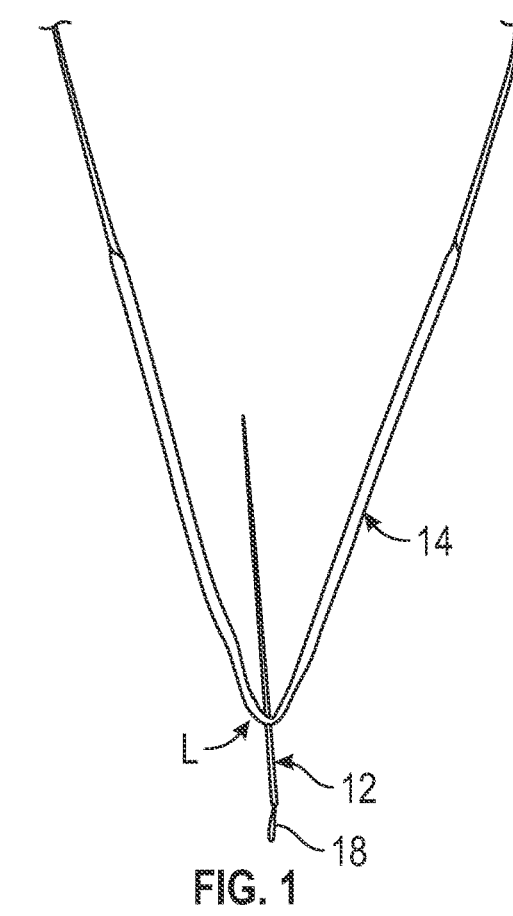
FIGS. 1, 2, 3, and 4 schematically illustrate the formation of an adjustable suture loop. The adjustable suture loop may be constructed and utilized as part of a surgical method for reattaching torn tissue to bone.

This disclosure is directed to adjustable tissue repair systems and surgical methods for repairing tissue defects within a joint. The system and methods described herein may be utilized to reduce, fixate, and compress tissue to bone. These and other features of this disclosure are described in further detail below.

An exemplary surgical method may include, inter alia, inserting a first suture anchor into a bone, passing a first suture of the first suture anchor through a tissue, feeding the first suture through a loop of a first adjustable suture loop, securing the first adjustable suture loop relative to the first suture anchor, connecting a first limb of the first adjustable suture loop to a second suture anchor, and inserting the second suture anchor into the bone at a position that is lateral to the first suture anchor.

In any further embodiment, the first adjustable suture loop includes the loop, the first limb, and a second limb.

In any further embodiment, the first limb is a slidable limb and the second limb is a static limb.

In any further embodiment, the method includes connecting the second limb to a third suture anchor, and inserting the third suture anchor into the bone at a location adjacent to the second suture anchor.

In any further embodiment, securing the first adjustable suture loop relative to the first suture anchor includes splicing the first suture through itself after feeding the first suture through the loop and through a shuttle device of the first suture anchor.

In any further embodiment, securing the first adjustable suture loop relative to the first suture anchor further includes tensioning the first suture to approximate the first adjustable suture loop against the tissue.

In any further embodiment, connecting the first limb of the first adjustable suture loop to the second suture anchor includes feeding the first limb through an eyelet of the second suture anchor.

In any further embodiment, inserting the second suture anchor into the bone includes positioning the eyelet within a socket formed in the bone, tensioning the first limb, and moving an anchor body of the second suture anchor toward the eyelet within the socket, thereby trapping the first limb between the bone and the anchor body.

In any further embodiment, the first suture anchor is part of a medial row of suture anchors and the second suture anchor is part of a lateral row of suture anchors. A crisscross suture pattern establishes a desired area of footprint compression over top of the tissue.

In any further embodiment, the first suture anchor and the second suture anchor are knotless suture anchors.

Another exemplary surgical method may include, inter alia, inserting a first suture anchor into a bone, passing a first suture of the first suture anchor through a tissue, feeding the first suture through a loop of a first adjustable suture loop, knotlessly securing the first adjustable suture loop relative to the first suture anchor, tensioning the first suture to approximate the first adjustable suture loop against the tissue, connecting a first limb of the first adjustable suture loop to a second suture anchor, and inserting the second suture anchor into the bone at a position that is lateral to the first suture anchor, thereby fixating the first limb relative to the bone such that the first limb extends over top of the tissue.

In any further embodiment, knotlessly securing the first adjustable suture loop relative to the first suture anchor includes splicing the first suture through itself after feeding the first suture through the loop and through a shuttle device of the first suture anchor.

In any further embodiment, tensioning the first suture to approximate the first adjustable suture loop against the tissue occurs after splicing the first suture through itself.

In any further embodiment, splicing the first suture through itself establishes a suture loop that is looped around the loop of the first adjustable suture loop.

In any further embodiment, tensioning the first suture pulls the tissue laterally over top of the first suture anchor.

In any further embodiment, the first suture anchor is a first knotless suture anchor that includes a shuttle device, and the second suture anchor is a second knotless suture anchor that includes an eyelet.

In any further embodiment, the method includes inserting a third suture anchor into the bone, passing a second suture of the third suture anchor through the tissue, feeding the second suture through a loop of a second adjustable suture loop, and knotlessly securing the second adjustable suture loop relative to the third suture anchor.

In any further embodiment, the method includes connecting a second limb of the second adjustable suture loop to the second suture anchor before inserting the second suture anchor into the bone.

In any further embodiment, the method includes connecting a third limb of the second adjustable suture loop to a fourth suture anchor, and inserting the fourth suture anchor into the bone at a position that is lateral to the third suture anchor.

An exemplary adjustable tissue repair system may include, inter alia, a first knotless suture anchor, a second knotless suture anchor, and an adjustable suture loop connected to both the first knotless suture anchor and the second knotless suture anchor. The adjustable suture loop includes a loop, a slidable limb, and a static limb.

FIGS. 1-22 schematically illustrate various aspects associated with a surgical method for attaching a tissue (e.g., ligament, tendon, graft, etc.) to a bone. The tissue may have torn away from bone during vigorous exercise or sporting activities, for example. When such tears occur, reattachment is often necessary to repair the tissue defect. Although the surgical method is described herein for reapproximating and fixating torn tissue back to bone, the surgical methods of this disclosure could be utilized to repair any type of tissue effect.

The surgical method schematically illustrated in FIGS. 1-22 could be used in conjunction with a variety of orthopedic surgical repairs, including but not limited to rotator cuff repairs, Achilles tendon repairs, patellar tendon repairs, ACL/PCL reconstructions, hip and shoulder reconstructions, among many others. The bone to which the tissue is reattached may therefore be associated with any joint of the human musculoskeletal system (e.g., shoulder, knee, hip, ankle, etc.).

In an embodiment, the surgical method described herein is performed as an arthroscopic procedure by working through various arthroscopic portals. However, the exemplary surgical method could alternatively be performed as an open procedure within the scope of this disclosure. As detailed below, the exemplary surgical method may be employed to reduce and then reattach tissue to bone in a manner that enhances footprint compression to maximize tissue-to-bone contact.

FIGS. 1-5 schematically illustrate exemplary preliminary steps of the surgical method for reattaching torn tissue to bone. The preliminary steps may be performed to create an adjustable suture loop 10 (see FIGS. 4 and 5) that can be utilized during subsequent steps of the surgical method.

Referring to FIG. 1, a needle 12 may be pierced through a suture strand 14 at a location L. The location L may be near a midspan of the length of the suture strand 14, for example. In an embodiment, the suture strand 14 is a suture tape, such as FiberTape®. FiberTape® is a suture product marketed and sold by Arthrex, Inc. However, other suture products could be utilized for the suture strand 14.

Figure 2:
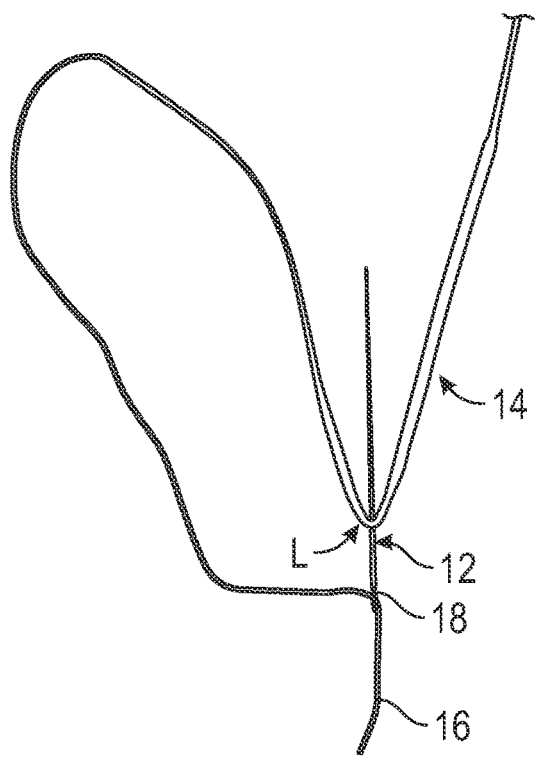
Figure 3:
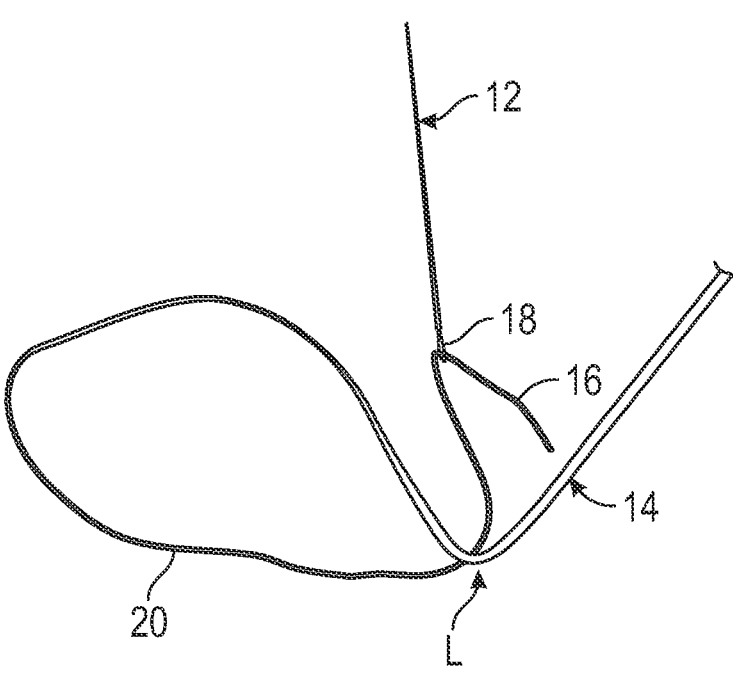
Figure 4:
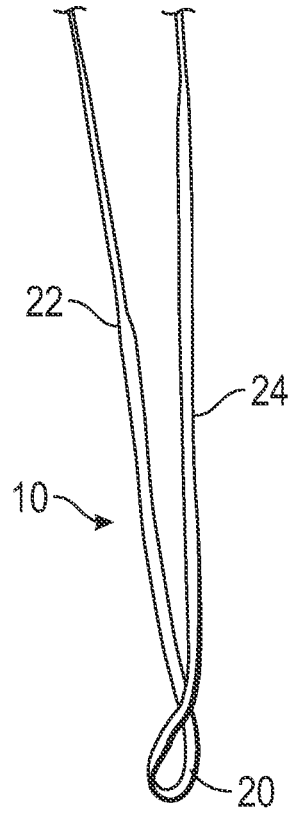

As shown in FIGS. 2 and 3, the needle 12 may be used to splice the suture strand 14 through itself at the location L. For example, a tail 16 of the suture strand 14 may be fed through an eyelet 18 of the needle 12, and the needle 12 may then be used to pull the tail 16 through the suture strand 14. The tail 16 may be pulled until a loop 20 of a desired size is formed in the suture strand 14. A slidable limb 22 and a static limb 24 extend from the loop 20. The slidable limb 22 may be tensioned or loosened to adjust the size of the loop 20. Together, the loop 20, the slidable limb 22, and the static limb 24 establish the adjustable suture loop 10 (see FIG. 4).

Figure 5:
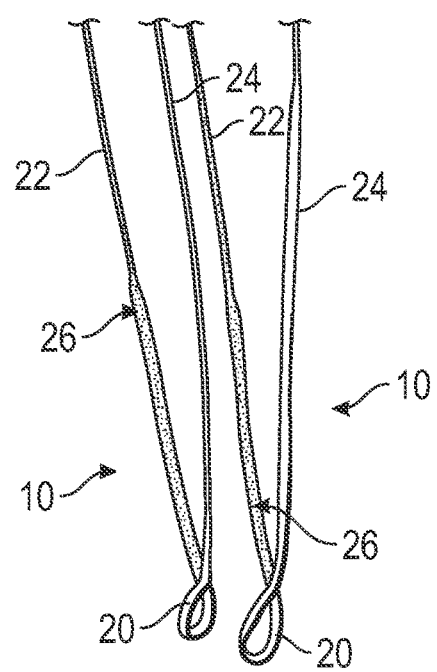
FIG. 5 illustrates multiple adjustable suture loops that can be utilized during a surgical method for reattaching torn tissue to bone.

Referring to FIG. 5, multiple adjustable suture loops 10 may be prepared in anticipation of using the adjustable suture loops 10 during subsequent steps of the surgical method. The slidable limb 22 of each adjustable suture loop 10 may optionally be colored (shown schematically at reference numeral 26) to help visually distinguish it from the static limb 24.

Figure 6:
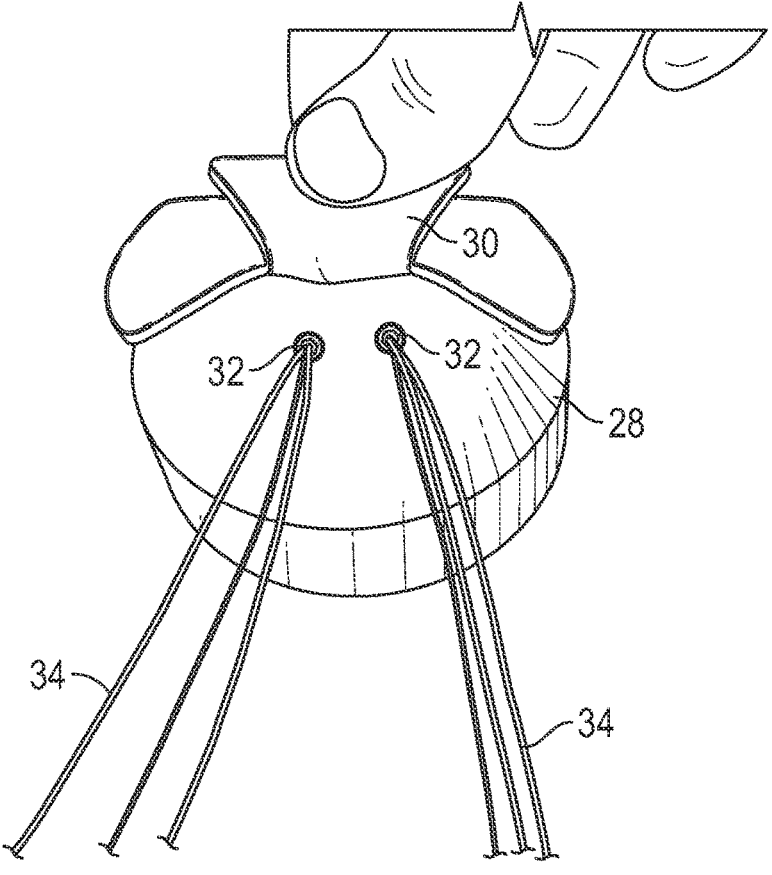
FIG. 6 schematically illustrates a step of a surgical method for reattaching torn tissue to bone.

Referring now to FIG. 6, after appropriately preparing a bone 28 (e.g., by debriding, creating a bleeding bone bed, preparing bone sockets, etc.) from which a tissue 30 has at least partially torn away from, a medial row of fixation devices may be implanted into the bone 28. The medial row of fixation devices may include one or more suture anchors 32. In an embodiment, the suture anchors 32 are knotless suture anchors that do not require the need to tie any knots in the various structures for reducing and securing the tissue 30 back to the bone 28. However, traditional knot tying style suture anchors could alternatively or additionally be used within the medial row of fixation devices.

In an embodiment, the suture anchors 32 of the medial row are placed at or near the articular margin of the bone 28. However, other implantation locations could be selected based on the performing surgeon's own preferences. Notably, although two suture anchors 32 are illustrated as being part of the medial row in the illustrated embodiment, a greater or fewer number of suture anchors could be utilized as part of the surgical method within the scope of this disclosure. For example, the medial row could include but a single suture anchor 32 in some implementations of the surgical method.

Each suture anchor 32 may be pre-loaded with one or more sutures 34. The sutures 34 may include individual suture strands, multiple suture strands, suture tape, or any other suture-like product. As shown in FIG. 7, the sutures 34 may be passed upwardly through the tissue 30 after each suture anchor 32 is adequately fixated within the bone 28. At this stage of the surgical method, the tissue 30 may or may not be directly over top of the suture anchors 32.

FIGS. 8-11 illustrate exemplary knotless suture anchors that can be utilized as the suture anchors 32 of the medial row of fixation devices when performing the surgical methods described herein. Knotless suture anchors similar to those shown in FIGS. 8-11 may be utilized either alone or in combination with one another as part of the medial row during the surgical method.

An exemplary knotless suture anchor 32-1 is illustrated in FIGS. 8 and 9. In this embodiment, the knotless suture anchor 32-1 is a "soft" anchor assembly made exclusively of soft, suture-based materials. The suture-based materials may include soft materials such as yarns, fibers, filaments, strings, fibrils, strands, sutures, etc., or any combination of such materials. The soft materials may be synthetic or natural materials, or combinations of synthetic and natural materials, and may be bio-degradable or non-degradable within the scope of this disclosure. The soft, suture-based materials allow the knotless suture anchor 32-1 to be inserted into bone sockets/holes and bunch together, collapse, expand and/or change shape to fixate within the socket/hole.

The knotless suture anchor 32-1 may include an anchor body 36-1 and a suture 34 received through the anchor body 36-1. A shuttle device 38 may be spliced through portions of the suture 34. The shuttle device 38 may be a passing wire or another suture, for example.

The anchor body 36-1 of the knotless suture anchor 32-1 may be inserted into a socket 40 formed in the bone 28 (see FIG. 9). The socket 40 may be a preformed opening formed in the bone 28 that is configured for receiving the anchor body 36-1.

The shuttle device 38 may be pre-assembled to the suture 34 as shown in FIG. 8, and the suture 34 may form a suture loop 42 after the suture 34 is shuttled through itself as shown in FIG. 9. For example, a suture tail 44 of the suture 34 may be passed through an eyelet 46 of the shuttle device 38 (in the direction of arrow A of FIG. 8), and then a free end 48 of the shuttle device 38 may be pulled (in the direction of arrow B of FIG. 8) to allow the suture 34 to pass through itself and form the suture loop 42. The perimeter of the suture loop 42 is adjustable to allow the construct to be self-cinching and to adjust the tension on the construct that is to be fixated.

In an exemplary embodiment, the suture anchors 32 of the medial row may include the design of the knotless suture anchor 32-1 for performing the surgical method steps herein. However, other type of suture anchors or combinations of suture anchors are contemplated within the scope of this disclosure.

Figure 10:
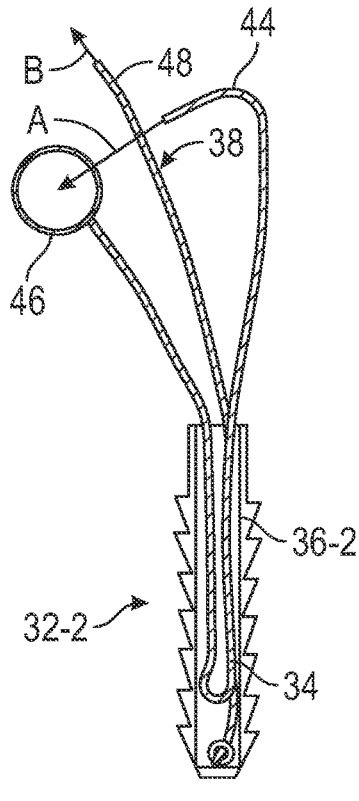
FIGS. 10 and 11 illustrate another exemplary knotless suture anchor.
Figure 11:
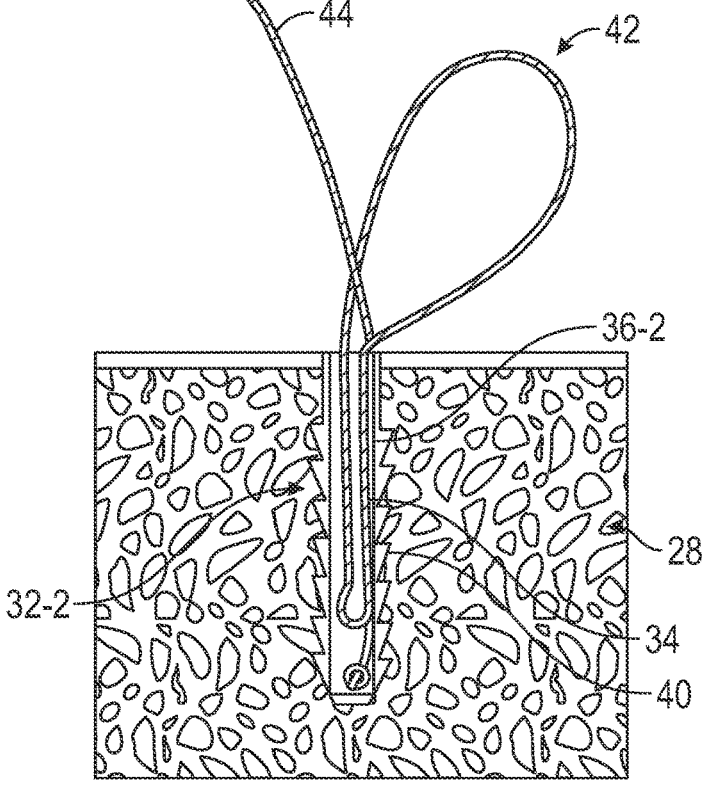

Another exemplary knotless suture anchor 32-2 is illustrated in FIGS. 10 and 11. The knotless suture anchor 32-2 may include an anchor body 36-2 and a suture 34 received through the anchor body 36-2. In this embodiment, the anchor body 36-2 is a relatively rigid plastic body, and the knotless suture anchor 32-2 is therefore not considered to be a "soft" anchor assembly.

The knotless suture anchor 32-2 may include a tensionable knotless mechanism that is similar to that of the knotless suture anchor 32-1. For example, a shuttle device 38 may be spliced through portions of the suture 34. The shuttle device 38 may be a passing wire or another suture, for example. The anchor body 36-2 of the knotless suture anchor 32-2 may be inserted into a socket 40 formed in the bone 28 (see FIG. 11). The socket 40 may be a preformed opening formed in the bone 28 that is configured for receiving the anchor body 36-2. The shuttle device 38 may be pre-assembled to the suture 34 as shown in FIG. 10 and may be utilized to form a suture loop 42 after the suture 34 is shuttled through itself as shown in FIG. 11. For example, a suture tail 44 of the suture 34 may be passed through an eyelet 46 of the shuttle device 38 (in the direction of arrow A of FIG. 10), and then a free end 48 of the shuttle device 38 may be pulled (in the direction of arrow B of FIG. 10) to allow the suture 34 to pass through itself and form the suture loop 42. The perimeter of suture loop 42 is adjustable to allow the construct to be self-cinching and to adjust the tension on the construct that is to be fixated by the knotless suture anchor 32-2.

In an exemplary embodiment, the suture anchors 32 of the medial row may include the design of the knotless suture anchor 32-2 (rather than that of the knotless suture anchor 32-1, for example) for performing the surgical method steps described herein. However, other type of suture anchors or combinations of suture anchors are contemplated within the scope of this disclosure.

Figure 12:
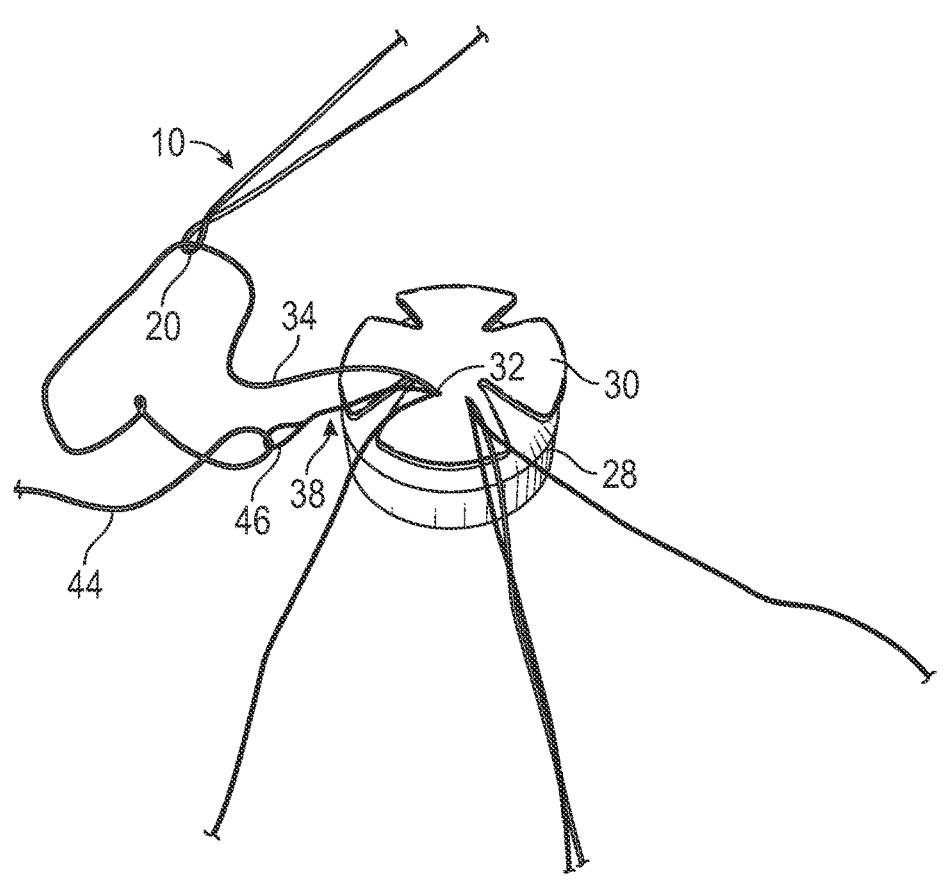
FIG. 12 illustrates another step of a surgical method for reattaching torn tissue to bone.
Figure 13:
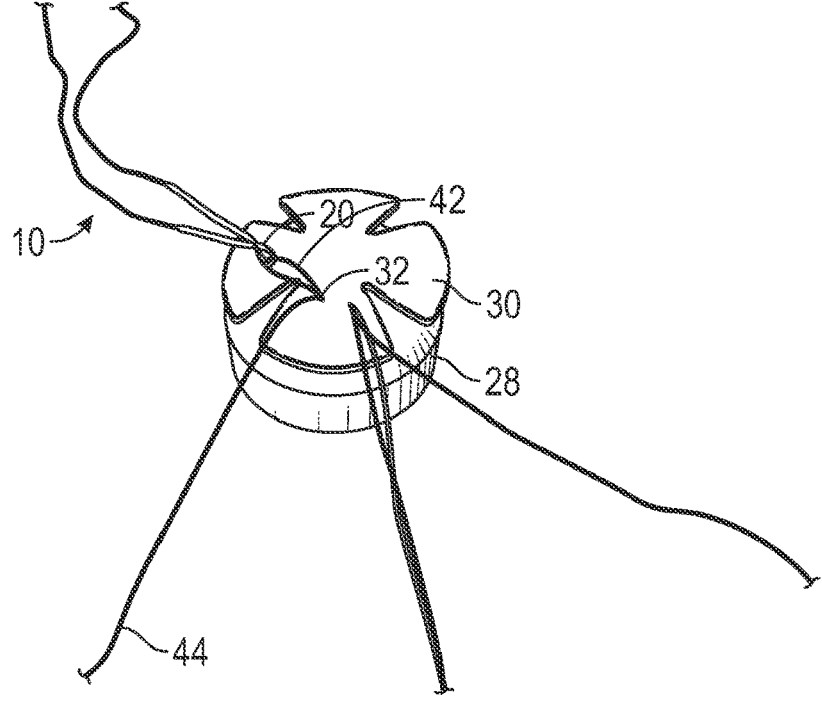
FIG. 13 illustrates another step of a surgical method for reattaching torn tissue to bone.
Figure 14:
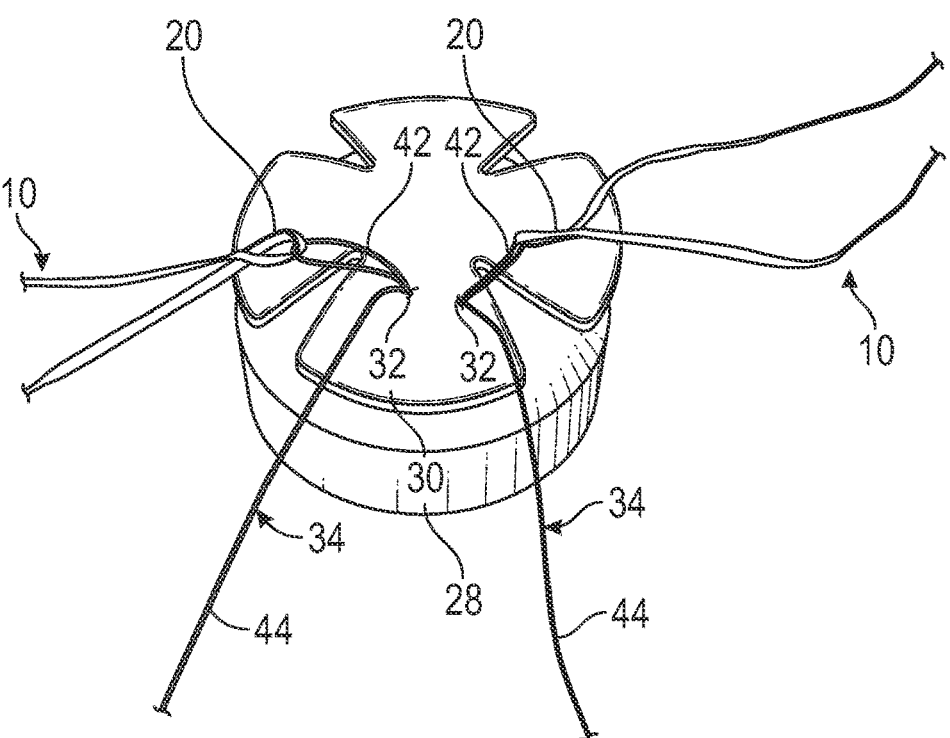
FIG. 14 illustrates another step of a surgical method for reattaching torn tissue to bone.

Referring next to FIGS. 12 and 13, the surgical method may continue by feeding the suture tail 44 of the suture 34 of one of the suture anchors 32 through the loop 20 of one of the adjustable suture loops 10 and then through the eyelet 46 of the shuttle device 38. The suture 34 may then be spliced through itself using the shuttle device 38 to form the suture loop 42 about the loop 20 of the adjustable suture loop 10. Splicing the suture 34 through itself in this manner may therefore approximate the adjustable suture loop 10 into a position over top of the tissue 30. This process may be repeated one or more times (see FIG. 14) depending on the number of suture anchors 32 used as part of the medial row.

Figure 15:
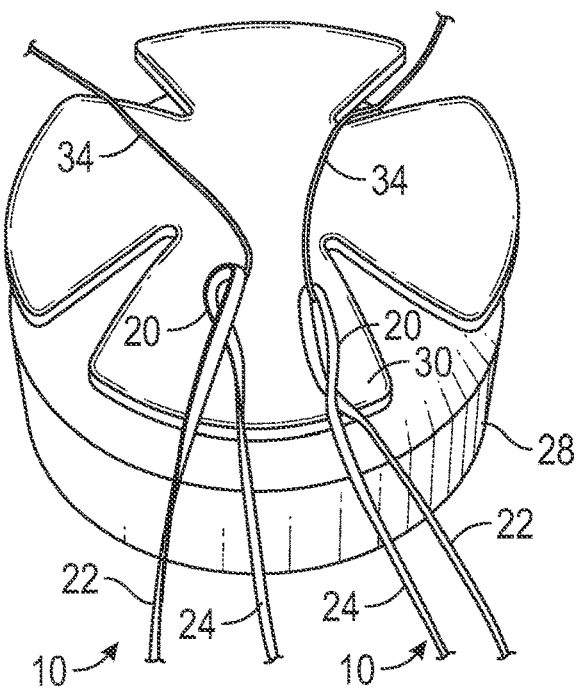
FIG. 15 illustrates another step of a surgical method for reattaching torn tissue to bone.
Figure 19:
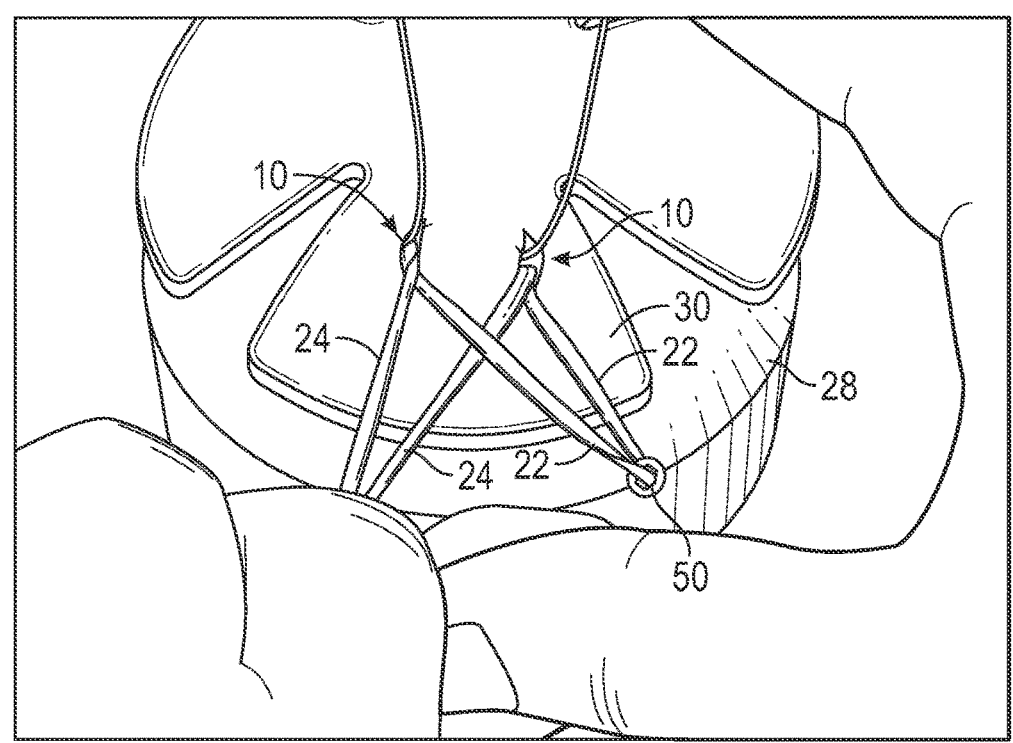
FIG. 19 illustrates another step of a surgical method for reattaching torn tissue to bone.

The sutures 34 may be further tensioned to approximate each adjustable suture loop 10 firmly against the tissue 30 (see FIG. 15). The tissue 30 therefore reduces into place over top of the suture anchors 32 (e.g., is pulled laterally) and is fixated against the bone 28. At this stage of the surgical method, the suture anchors 32 are located fully underneath the tissue 30. Further, the adjustable suture loops 10 can still be tightened or loosened using the slidable limbs 22 and the static limbs 24 at this stage of the surgical method.

As shown beginning at FIG. 16, the surgical method can next proceed by implanting a lateral row of fixation devices into the bone 28. The lateral row of fixation devices may include one or more suture anchors 50. In an embodiment, the suture anchors 50 of the lateral row are placed laterally from the medial row of suture anchors 32 and slightly distal to the greater tuberosity of the bone 28. However, other implantation locations could be selected based on the performing surgeon's own preferences and depending on the type of orthopedic procedure being performed. In an embodiment, the suture anchors 50 are knotless suture anchors that do not require the need to tie any knots in the various structures for achieving fixation.

The suture anchors 50 of the lateral row may be implanted into the bone 28 after connecting one or more limbs of the adjustable suture loops 10 to the suture anchors 50. The suture anchors 50 may be implanted after connecting the adjustable suture loops 10 thereto by employing the design of another exemplary knotless suture anchor 32-3 shown in FIGS. 17-18. The knotless suture anchor 32-3 may include an anchor body 52 and an eyelet 54. In this embodiment, the anchor body 52 and the eyelet 54 are relatively rigid plastic structures, and thus the knotless suture anchor 32-3 is not considered to be a "soft" anchor assembly.

The anchor body 52 may be pre-loaded onto a driver 56. The anchor body 52 may be configured as a screw or an interference plug that is appropriately cannulated for receiving a shaft 58 of the driver 56. The eyelet 54 may be provided at a distal end 60 of the driver 56. The eyelet 54 may be releasably attached to the distal end 60 and may include an aperture 62 for receiving one or more sutures or other thread-like materials.

The anchor body 52 and the eyelet 54 of the knotless suture anchor 32-3 may be inserted into a socket 40 formed in the bone 28 (see FIG. 18). The socket 40 may be a preformed opening formed in the bone 28 that is configured for receiving the anchor body 52 and the eyelet 54. One or more of the slidable limbs 22 and/or the static limbs 24 of one or more of the adjustable suture loops 10 may be loaded through the eyelet 54, and then the eyelet 54 may be inserted down into the socket 40. The limb(s) 22, 24 may then be tensioned prior to moving the anchor body 52 down toward the eyelet 54 within the socket 40. Once implanted within the socket 40, the anchor body 52 may trap the limb(s) 22, 24 between the bone 28 and the anchor body 52 in order to fixate the limb(s) 22, 24 in place. In this way, the knotless suture anchor 32-3 provides the ability to implant the lateral row of suture anchors 50 after making the connection to the adjustable suture loop 10 during the surgical method.

Referring again to FIG. 16, the slidable limb 22 from each adjustable suture loop 10 may be fed through the eyelet 54 of one of the suture anchors 50 of the lateral row (in this example, the anterior suture anchor 50). The slidable limbs 22 may then be tensioned prior to and/or during the positioning of the eyelet 54 within the socket 40 formed in the bone 28. An elongated shaft 64, such as that of a suture anchor inserter, may be used to intentionally leave a small amount of slack in the medial-to-lateral fixation. The anchor body 52 may then be moved into the socket 40, thereby trapping the slidable limbs 22 in place in order to become fixated relative to the bone 28. The static limb 24 from each adjustable suture loop 10 may then be tensioned to remove any slack from the initial side (here, the anterior side) of the fixation (see FIG. 19). During this tensioning, the adjustable suture loops 10 may act as pulleys to balance the tension between the slidable limbs 22.

Figure 20:
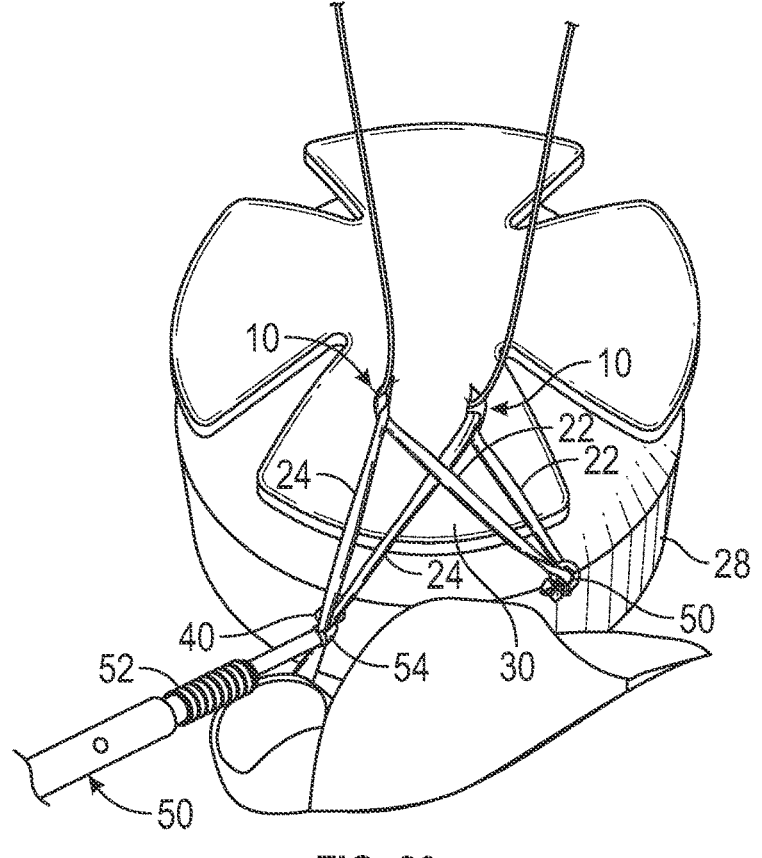
FIG. 20 illustrates another step of a surgical method for reattaching torn tissue to bone.

Referring next to FIG. 20, the static limb 24 from each adjustable suture loop 10 may be fed through the eyelet 54 of another one of the suture anchors 50 of the lateral row (in this example, the posterior suture anchor 50). The static limbs 24 may then be tensioned prior to and/or during the positioning of the eyelet 54 within the socket 40 formed in the bone 28. The anchor body 52 may then be moved into the socket 40, thereby trapping the static limbs 24 in place in order to become fixated relative to the bone 28 (see FIG. 21).

Figure 21:
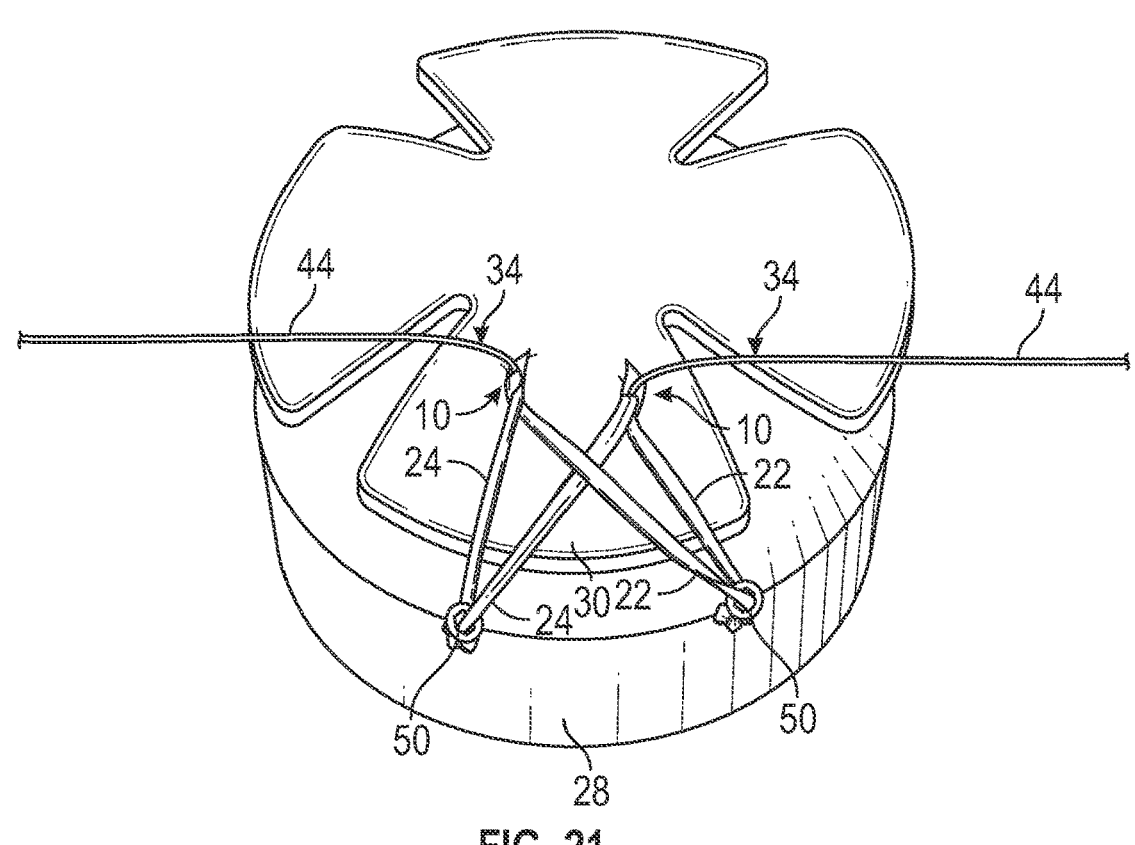
FIG. 21 illustrates yet another step of a surgical method for reattaching torn tissue to bone.

Referring to FIG. 21, the suture tails 44 of the sutures 34 of the suture anchors 32 of the medial row may optionally be tensioned at this point of the surgical method if more tension is desired. The sutures 34 may act as pulleys, thereby evenly pulling all limbs 22, 24 of the adjustable suture loops 10. The suture tails 44 and the free ends of the limbs 22, 24 may then be trimmed to complete the surgical method.

Figure 22:
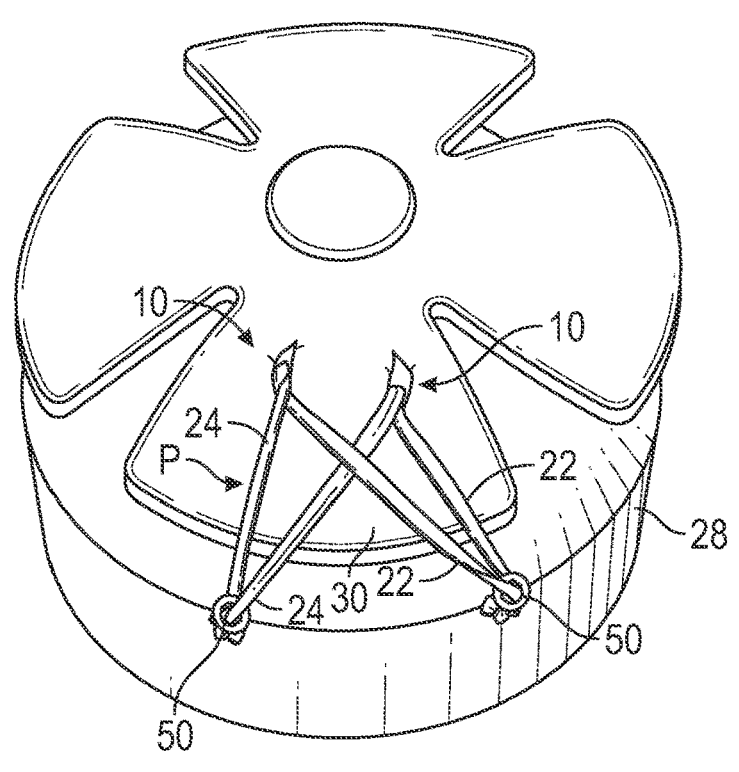
FIG. 22 illustrates a final repair construct of a surgical method for reattaching tissue to bone.

The final construct achieved by the surgical method is shown in FIG. 22. The limbs 22, 24 may be arranged in various bridging configurations between the adjustable suture loops 10 and the suture anchors 50 of the lateral row. For example, as shown in FIG. 22, the limbs 22, 24 may be arranged in a crisscross pattern P that provides a desired area of footprint compression over top of the tissue 30. Any bridging configuration using any number of suture anchors and adjustable suture loops can be achieved as part of the surgical method.

In the above embodiments, the limbs 22, 24 of the adjustable suture loops 10 are connected to the suture anchors 50 of the lateral row before implanting the suture anchors 50 into the bone 28. However, other implementations are possible. For example, the suture anchors 50 could be implanted before making the connection to the adjustable suture loops 10, such as by employing the design of the knotless suture anchor 32-1 or 32-2, for example.

Figure 23:
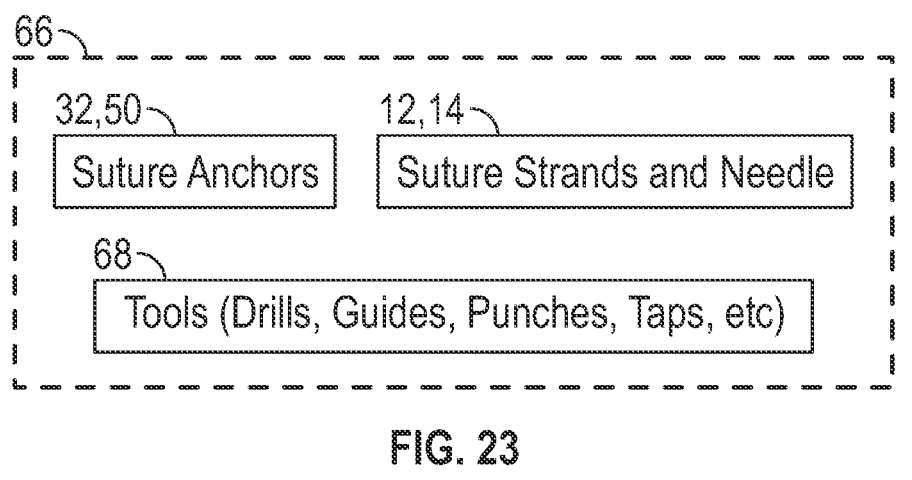

FIG. 23 schematically illustrates an exemplary tissue fixation system 66 that may be provided for performing the surgical method described above. The tissue fixation system 66 may be provided in the form of a surgical kit that includes all the necessary tools and components for performing surgical methods for reducing and reattaching torn tissue to bone. In an embodiment, the tissue fixation system 66 may include at least the following components:

1. At least (4) suture anchors 32, 50;
2. At least two suture strands 14 and at least one needle 12 for forming the adjustable suture loops 10; and
3. Various tools 68 (e.g., disposable drills, drill guides, punches, taps, etc.) for inserting the suture anchors 32, 50 into bone.

Other components or different combinations of components could be provided as part of the tissue fixation system 66 within the scope of this disclosure. For example, the tissue fixation system 66 could include various templates, scorers, curettes, and/or measuring devices that may be utilized to help prepare the tissue 30 and the bone 28 for performing the surgical methods discussed herein.

The tissue fixation systems and surgical methods described herein may be utilized to approximate, fixate, and compress tissue to bone. The proposed systems and methods provide a multi-point fixation configuration for fixating tissue to bone. The use of adjustable suture loops in combination with medial and lateral suture anchors provides a relatively stiff construct for maintaining footprint compression, thereby maximizing tissue-to-bone contact.

Although the different non-limiting embodiments are illustrated as having specific components or steps, the embodiments of this disclosure are not limited to those particular combinations. It is possible to use some of the components or features from any of the non-limiting embodiments in combination with features or components from any of the other non-limiting embodiments.

It should be understood that like reference numerals identify corresponding or similar elements throughout the several drawings. It should further be understood that although a particular component arrangement is disclosed and illustrated in these exemplary embodiments, other arrangements could also benefit from the teachings of this disclosure.

The foregoing description shall be interpreted as illustrative and not in any limiting sense. A worker of ordinary skill in the art would understand that certain modifications could come within the scope of this disclosure. For these reasons, the following claims should be studied to determine the true scope and content of this disclosure.

What is claimed is:

1. A surgical method, comprising:
inserting a first suture anchor into a bone;
passing a first suture of the first suture anchor through a tissue;
after inserting the first suture anchor into the bone and passing the first suture through the tissue, feeding the first suture through a loop of a first adjustable suture loop;
securing the first adjustable suture loop relative to the first suture anchor;
connecting a first limb of the first adjustable suture loop to a second suture anchor; and
inserting the second suture anchor into the bone at a position that is lateral to the first suture anchor.

2. The surgical method as recited in claim 1, wherein the first adjustable suture loop includes the loop, the first limb, and a second limb.

3. The surgical method as recited in claim 2, wherein the first limb is a slidable limb and the second limb is a static limb.

4. The surgical method as recited in claim 2, comprising:
connecting the second limb to a third suture anchor; and
inserting the third suture anchor into the bone at a location adjacent to the second suture anchor.

5. The surgical method as recited in claim 1, wherein securing the first adjustable suture loop relative to the first suture anchor includes:
splicing the first suture through itself after feeding the first suture through the loop and through a shuttle device of the first suture anchor.

6. The surgical method as recited in claim 5, wherein securing the first adjustable suture loop relative to the first suture anchor further includes:
tensioning the first suture to approximate the first adjustable suture loop against the tissue.

7. The surgical method as recited in claim 1, wherein connecting the first limb of the first adjustable suture loop to the second suture anchor includes:
feeding the first limb through an eyelet of the second suture anchor.

8. The surgical method as recited in claim 7, wherein inserting the second suture anchor into the bone includes:
positioning the eyelet within a socket formed in the bone;
tensioning the first limb; and
moving an anchor body of the second suture anchor toward the eyelet within the socket, thereby trapping the first limb between the bone and the anchor body.

9. The surgical method as recited in claim 1, wherein the first suture anchor is part of a medial row of suture anchors and the second suture anchor is part of a lateral row of suture anchors, and further wherein a crisscross suture pattern establishes a desired area of footprint compression over top of the tissue.

10. The surgical method as recited in claim 1, wherein the first suture anchor and the second suture anchor are knotless suture anchors, and the first suture anchor includes a different knotless suture anchor design from the second suture anchor.

11. The surgical method as recited in claim 1, wherein the first adjustable suture loop is not directly connected to an anchor body of either the first suture anchor or the second suture anchor.

12. The surgical method as recited in claim 1, wherein the first adjustable suture loop is knotlessly fixated to both the first suture anchor and the second suture anchor.

13. A surgical method, comprising:
inserting a first suture anchor into a bone;
passing a first suture of the first suture anchor through a tissue;
after inserting the first suture anchor into the bone and passing the first suture through the tissue, feeding the first suture through a loop of a first adjustable suture loop;
knotlessly securing the first adjustable suture loop relative to the first suture anchor;
tensioning the first suture to approximate the first adjustable suture loop against the tissue;
connecting a first limb of the first adjustable suture loop to a second suture anchor; and
inserting the second suture anchor into the bone at a position that is lateral to the first suture anchor, thereby fixating the first limb relative to the bone such that the first limb extends over top of the tissue.

14. The surgical method as recited in claim 13, wherein knotlessly securing the first adjustable suture loop relative to the first suture anchor includes:
splicing the first suture through itself after feeding the first suture through the loop and through a shuttle device of the first suture anchor.

15. The surgical method as recited in claim 14, wherein tensioning the first suture to approximate the first adjustable suture loop against the tissue occurs after splicing the first suture through itself.

16. The surgical method as recited in claim 14, wherein splicing the first suture through itself establishes a suture loop that is looped around the loop of the first adjustable suture loop.

17. The surgical method as recited in claim 13, wherein tensioning the first suture pulls the tissue laterally over top of the first suture anchor.

18. The surgical method as recited in claim 13, wherein the first suture anchor is a first knotless suture anchor that includes a shuttle device and the second suture anchor is a second knotless suture anchor.

19. The surgical method as recited in claim 13, comprising:
inserting a third suture anchor into the bone;
passing a second suture of the third suture anchor through the tissue;
feeding the second suture through a loop of a second adjustable suture loop; and
knotlessly securing the second adjustable suture loop relative to the third suture anchor.

20. The surgical method as recited in claim 19, comprising:

connecting a second limb of the second adjustable suture loop to the second suture anchor before inserting the second suture anchor into the bone.

21. The surgical method as recited in claim 20, comprising:

connecting a third limb of the second adjustable suture loop to a fourth suture anchor; and inserting the fourth suture anchor into the bone at a position that is lateral to the third suture anchor.

22. A surgical method, comprising:

inserting a first suture anchor into a bone;

passing a first suture of the first suture anchor through a tissue;

after inserting the first suture anchor into the bone and passing the first suture through the tissue, feeding the first suture through a loop of a first adjustable suture loop;

after feeding the first suture through the loop of the first adjustable suture loop, feeding the first suture through a shuttle device of the first suture anchor;

after feeding the first suture through the shuttle device, tensioning a free end of the shuttle device to splice the first suture through itself and thereby knotlessly secure the first adjustable suture loop relative to the first suture anchor;

tensioning the first suture to approximate the first adjustable suture loop against the tissue;

connecting a first limb of the first adjustable suture loop to a second suture anchor; and after connecting the first limb to the second suture anchor, inserting the second suture anchor into the bone at a position that is lateral to the first suture anchor, thereby fixating the first limb relative to the bone such that the first limb extends over top of the tissue.

* * * * *